(12) United States Patent
Conde

(10) Patent No.: US 6,624,323 B1
(45) Date of Patent: Sep. 23, 2003

(54) PROCESS AND INTERMEDIATES FOR MAKING 4-CYANOSUBSTITUTED CYCLOHEXANOIC ACIDS

(75) Inventor: Jose J. Conde, Radnor, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/088,178

(22) PCT Filed: Sep. 15, 2000

(86) PCT No.: PCT/US00/25379

§ 371 (c)(1),
(2), (4) Date: Mar. 14, 2002

(87) PCT Pub. No.: WO01/19785

PCT Pub. Date: Mar. 22, 2001

Related U.S. Application Data

(60) Provisional application No. 60/154,084, filed on Sep. 15, 1999.

(51) Int. Cl.$^7$ ..................... C07C 255/00; C07C 253/00
(52) U.S. Cl. ...................... 558/426; 558/332; 558/335; 558/346
(58) Field of Search ................................ 558/332, 335, 558/346, 426

(56) References Cited

FOREIGN PATENT DOCUMENTS

| WO | WO 95/03794 A1 | * | 2/1995 |
|----|----------------|---|--------|
| WO | WO 95/09623 A1 | * | 4/1995 |
| WO | WO95/24381 | | 9/1995 |

OTHER PUBLICATIONS

Agami et al, Kinetics and Mechanism of the Conjugate Hydrocyanation of alpha, beta –Unsaturated Ketones by the Potassium Cyanide–Ammonium Chloride System, 1982, Journal of Organic Chemistry, 47, pp. 3561–3563.*

* cited by examiner

*Primary Examiner*—Johann Richter
*Assistant Examiner*—Paul A. Zucker
(74) *Attorney, Agent, or Firm*—James M. Kanagy; Stephen Venetianer; Charles M. Kinzig

(57) ABSTRACT

Herein is provided a process for preparing substituted cyclohexanoic acids of formula (I), where $R_a$ is a carbon-containing group optionally linked by oxygen, sulfur or nitrogen to the phenyl ring and j is 1–5; and one of R and R* is hydrogen and the other is C(O)OH.

6 Claims, No Drawings

PROCESS AND INTERMEDIATES FOR MAKING 4-CYANOSUBSTITUTED CYCLOHEXANOIC ACIDS

This application is a 371 of PCT/US00/25379 filed Sep. 15, 2000 which claim s benefit of US provisional application 60/154,084 filed Sep. 15, 1999.

AREA OF THE INVENTION

This invention relates to a method for preparing certain acids which are useful as phosphodiesterase 4 inhibitors. More specifically, this invention relates to preparing 4-(substituted-phenyl)-4-cyanocyclohexanoic acids from guaiacol and certain intermediates prepared and used in that process.

BACKGROUND OF THE INVENTION

The process of this invention relates to making compounds which are useful in treating diseases modulated by the isoforms of the phosphodiesterase 4 enzyme. Guaiacol, the starting material, undergoes a series of nine transformations to provide a 4-cyanocyclohexanoic acid which, among several possible products, can be used to make certain PDE 4 inhibitors which are useful for treating pulmonary diseases such as chronic obstructive pulmonary disease (COPD) and asthma, and other diseases. The instant process can be used to make other 4-cyanocyclohexanoic acids as well.

The primary target compounds which are prepared by the methods of this invention and the intermediates disclosed herein are disclosed and described in U.S. Pat. No. 5,554,238 issued Sep. 3, 1996 and related patents and published applications. That patent is incorporated herein by reference in full. Those compounds, particularly the 4-cyanocyclohexanoic acids, have marked effects on neutrophil activity and inhibit neutrophil chemotaxis and degranulation in vitro. In animal models, those compounds reduce neutrophil extravasation from the circulation, pulmonary sequestration and the edematous responses to a number of inflammatory insults in vitro. They have been found to be useful in treating COPD in humans, and possibly in other mammalian species which suffer from COPD.

SUMMARY OF THE INVENTION

In a first aspect this invention relates to a process for preparing substituted cyclohexanoic acids of formula (I)

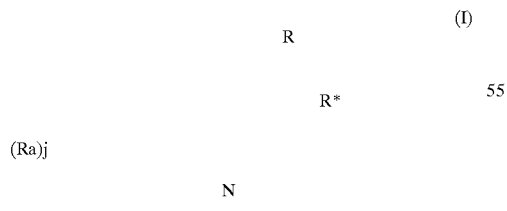

(I)

where $R_a$ is a carbon-containing group optionally linked by oxygen, sulfur or nitrogen to the phenyl ring and j is 1–5: and one of R and R* is hydrogen and the other is C(O)OH; which process comprises:
catalytically reducing a ketone of formula II

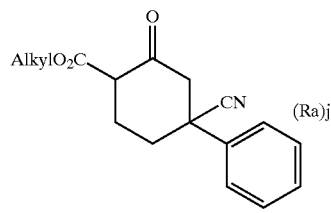

(II)

where alkyl has 1–6 carbon atoms and (Ra)j is the same as defined above, using a heavy metal catalyst and hydrogen gas.

More particularly this invention relates to a process for preparing compounds of formula IA

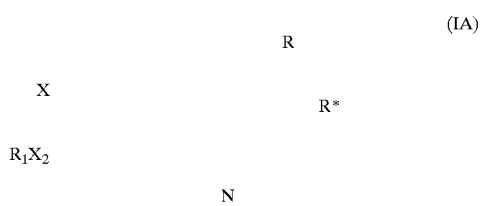

(IA)

wherein:

$R_1$ is —$(CR_4R_5)_rR_6$ wherein the alkyl moieties are unsubstituted or substituted with one or more halogens;

r is 0 to 6;

$R_4$ and $R_5$ are independently selected hydrogen or $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety is unsubstituted or substituted by 1 to 3 methyl groups, one ethyl group, or an hydroxyl group:

provided that:
b) when $R_6$ is hydroxyl, then r is 2 to 6; or
d) when $R_6$ is 2-tetrahydropyranyl, 2-tetrahydrothiopyranyl, 2-tetrahydrofuranyl, or 2-tetrahydrothienyl, then r is 1 to 6;

X is $YR_2$;

Y is O;

$X_2$ is O;

$R_2$ is —$CH_3$ or —$CH_2CH_3$, unsubstituted or substituted by 1 or more halogens;

one of R and R* is hydrogen and the other is C(O)OH.

In yet a further aspect, this invention relates to intermediates which are useful for preparing formula (I) compounds, namely, formula (A)

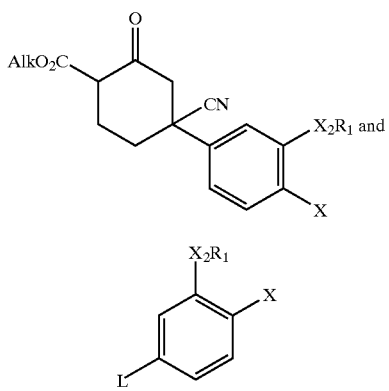

formula (C)

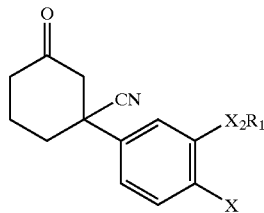

wherein, in each of formulas (A) and (C) and the X, $X_2$ and $R_1$ groups are the same as for formula (I) and L is a leaving group like halogen or a triflate.

In addition, this invention relates to a product of formula (I) as defined above made by the process of catalytically reducing a ketone of formula A using a heavy metal catalyst and hydrogen gas (A)

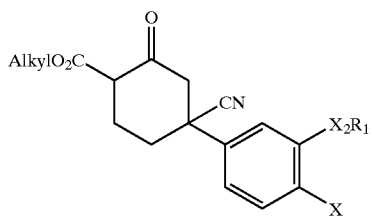

where alkyl has 1–6 carbon atoms and X, $X_2$ and $R_1$ arc the same as defined above.

In yet another aspect, this invention involves a product of formula (I) as defined above made by the process of carbonylating a ketone of formula (B)

(B)

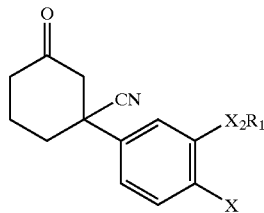

to form a compound of formula (A) and thereafter converting it to a compound of formula (I).

DETAILED DESCRIPTION OF THE INVENTION

This invention provides a means for preparing cyclohexanoic acids. In particular it relates to a method for preparing cyclohexanoic acids which are phosphodiesterase 4 inhibitors as more fully disclosed in U.S. Pat. No. 5,554,238, which is incorporated herein by reference. The invention can also be used to prepare other cyclohexanoic acids in addition to the ones illustrated herein.

As regards the preferred substituents on formulas (I), (II), (A), (B) and (C), for $R_1$ they are $CH_2$-cyclopropyl or $C_{4-6}$ cycloalkyl. Preferred $R_2$ groups are a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or a fluoro-substituted alkyl group, specifically a $C_{1-2}$ alkyl such as a —$CF_3$, —$CHF_2$, or —$CH_2CHF_2$. Most preferred are the —$CHF_2$ and —$CH_3$ moieties. Most preferred are those compounds wherein $R_1$ is —$CH_2$-cyclopropyl, cyclopentyl, 3-hydroxycyclopentyl, methyl or $CHF_2$ and $R_2$ is $CF_2H$ or $CH_3$. Particularly preferred are those compounds where $R_1$ is cyclopentyl and $R_2$ is $CH_3$.

The most preferred product made by the process of this invention is cis-[4-cyano-4-(3-cyclopentyloxy-4-methoxyphenyl)cyclohexane-1-carboxylic acid].

As regards intermediates, the L group of formula (C) is any leaving group which is reactive under the general set of conditions described in Example 3 below. Preferably L is a halogen or a triflate, and most perferable Cl, Br, or I, or a triflate.

When forming the cyclohexanone from the cyclohex-2-ene-1-one, a quaternary ammonium compound or quaternary amine and a cyanide salt are used. Examplary quaternary ammonium compounds are the ammonium halides such as ammonium chloride and ammonium bromide. Exemplary quaternary amines are the trialkylamine hydrohalides such as trimethylamine hydrochloride. Cyanide salts include the halide salts such as sodium or potassium cyanide.

Scheme I illustrates the conversion of guaiacol to the acid of Formula (I).

Scheme 1

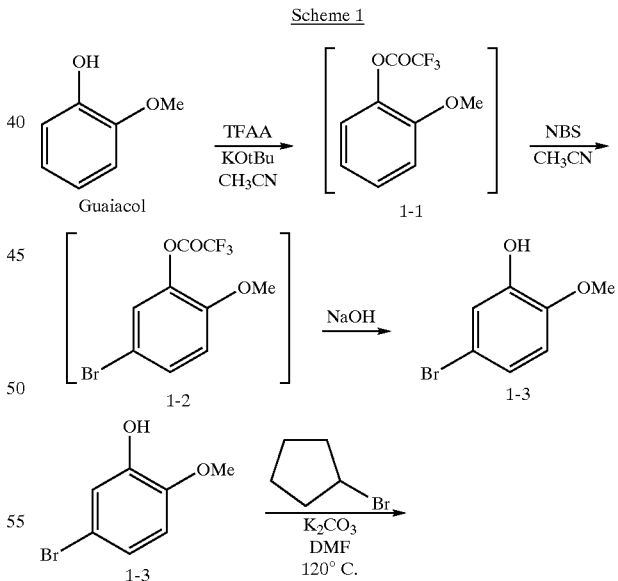

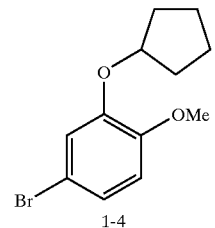

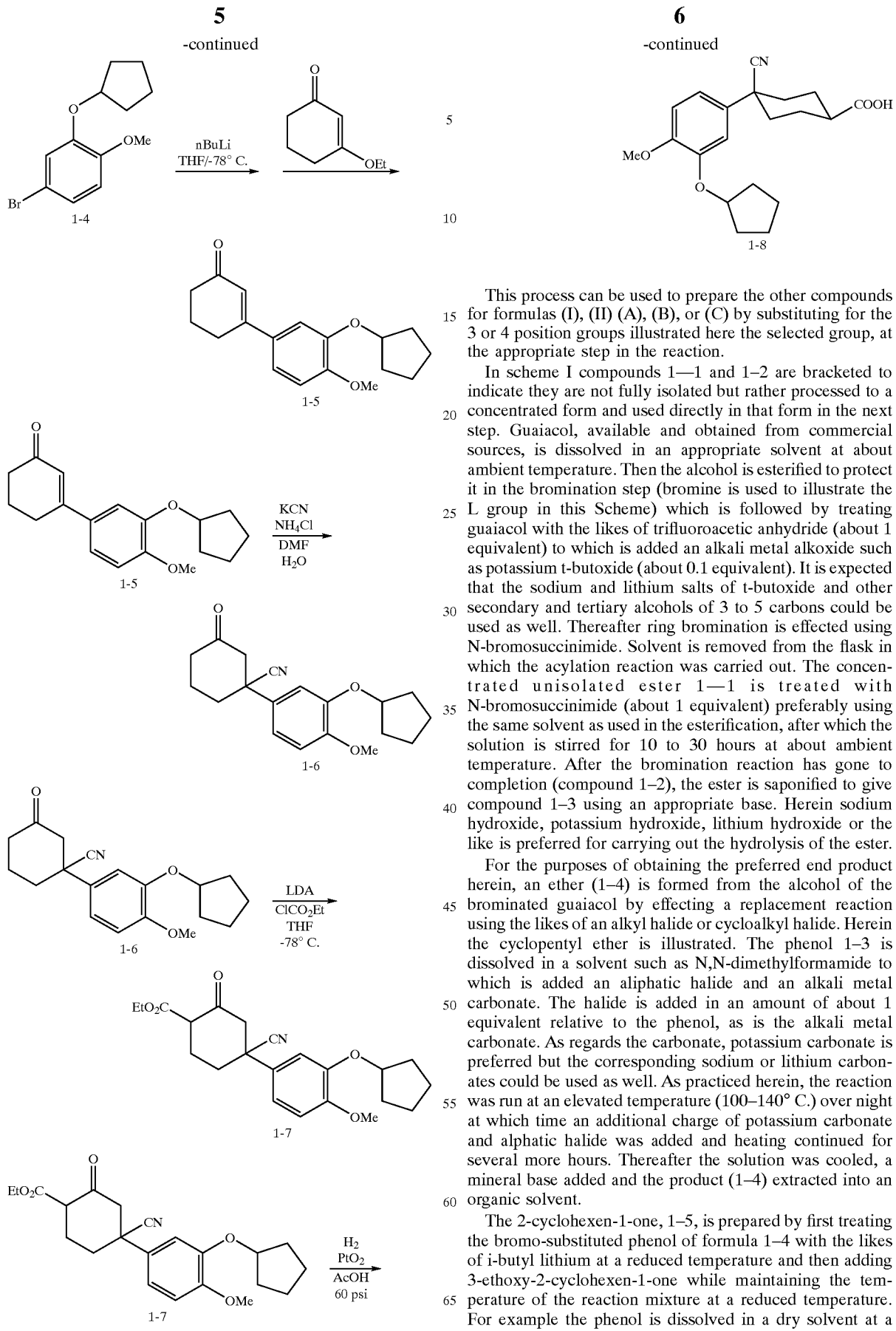

This process can be used to prepare the other compounds for formulas (I), (II) (A), (B), or (C) by substituting for the 3 or 4 position groups illustrated here the selected group, at the appropriate step in the reaction.

In scheme I compounds 1—1 and 1–2 are bracketed to indicate they are not fully isolated but rather processed to a concentrated form and used directly in that form in the next step. Guaiacol, available and obtained from commercial sources, is dissolved in an appropriate solvent at about ambient temperature. Then the alcohol is esterified to protect it in the bromination step (bromine is used to illustrate the L group in this Scheme) which is followed by treating guaiacol with the likes of trifluoroacetic anhydride (about 1 equivalent) to which is added an alkali metal alkoxide such as potassium t-butoxide (about 0.1 equivalent). It is expected that the sodium and lithium salts of t-butoxide and other secondary and tertiary alcohols of 3 to 5 carbons could be used as well. Thereafter ring bromination is effected using N-bromosuccinimide. Solvent is removed from the flask in which the acylation reaction was carried out. The concentrated unisolated ester 1—1 is treated with N-bromosuccinimide (about 1 equivalent) preferably using the same solvent as used in the esterification, after which the solution is stirred for 10 to 30 hours at about ambient temperature. After the bromination reaction has gone to completion (compound 1–2), the ester is saponified to give compound 1–3 using an appropriate base. Herein sodium hydroxide, potassium hydroxide, lithium hydroxide or the like is preferred for carrying out the hydrolysis of the ester.

For the purposes of obtaining the preferred end product herein, an ether (1–4) is formed from the alcohol of the brominated guaiacol by effecting a replacement reaction using the likes of an alkyl halide or cycloalkyl halide. Herein the cyclopentyl ether is illustrated. The phenol 1–3 is dissolved in a solvent such as N,N-dimethylformamide to which is added an aliphatic halide and an alkali metal carbonate. The halide is added in an amount of about 1 equivalent relative to the phenol, as is the alkali metal carbonate. As regards the carbonate, potassium carbonate is preferred but the corresponding sodium or lithium carbonates could be used as well. As practiced herein, the reaction was run at an elevated temperature (100–140° C.) over night at which time an additional charge of potassium carbonate and alphatic halide was added and heating continued for several more hours. Thereafter the solution was cooled, a mineral base added and the product (1–4) extracted into an organic solvent.

The 2-cyclohexen-1-one, 1–5, is prepared by first treating the bromo-substituted phenol of formula 1–4 with the likes of i-butyl lithium at a reduced temperature and then adding 3-ethoxy-2-cyclohexen-1-one while maintaining the temperature of the reaction mixture at a reduced temperature. For example the phenol is dissolved in a dry solvent at a temperature of about −78° C. and n-butyl lithium is added.

After a brief period of mixing, about 1 equivalent of the ketone is added, slowly. After a further brief mixing period, up to 20 minutes, aqueous mineral acid is added and the product is extracted into an appropriate organic solvent.

The cyano group is then introduced onto the cyclohexane ring on the same carbon on which the phenyl ring is substituted. This is accomplished by treating the 2-cyclohexene-1-one with a quaternary ammonium compound and an alkali metal cyanide salt in a compatible solvent and heating the reaction vessel for 24 to 72 hours at a mildly elevated temperature, but one below the boiling point of the solvent. By way of further illustration, the ketone is dissolved in an amine or amide solvent such as N,N-dimethylformamide at room temperature. Then a quaternary ammonium compound like ammonium chloride or trimethylamine hydrochloride is added along with potassium cyanide. This solution is then heated to about 90 to 120° C., (110° C. for DMF) for about 48 hours. The product, 1–6, is isolated using standard procedures.

A carboxyl group is then introduced onto the cyclohexane ring at the 6 position by treating the ketone with lithium N,N-diisopropylamide and then a chloro orthoformate such as chloroethylorthoformate. A slight excess of the amide and the orthoformate is added in sequence of a cooled solution of the ketone. The reaction is carried out at reduced temperature, preferably at about −78° C. After a brief period for the reaction to be effected, about 10 to 60 minutes, the reaction is quenched with water. Product, illustrated by 1–7 in scheme I, is recovered by conventional methods.

Reduction of the beta-keto ester, 1–7, is effected by hydrogenating the ketone using a heavy metal catalyst. Herein the catalyst is exemplified by platinum dioxide. Other metal catalysts such as palladium hydroxide can be used as well. The ketone is taken up in a solvent such as a volatile fatty acid, acetic acid for example, the catalyst added and the suspension put under several atmospheres of hydrogen. The resulting product is the cis form of [4-cyano-4-(3-cyclopentyloxy-4-methoxyphenyl)cyclohexane-1-carboxylic acid], The following examples are provided to illustrate the invention. These examples are not intended to limit the invention claimed herein, only to illustrate what may be claimed as the invention. What is reserved to the inventors is defined in the claims appended hereto.

SPECIFIC EXAMPLES

Example 1

Preparation of 5-Bromo-2-methoxyphenol

To a solution of guaiacol (5.0 g, 0.04 mol) in acetonitrile (50 ml) at ambient temperature, was added trifluoroacetic anhydride (6.2 ml, 1.1 eq.). The solution was stirred for 5 min., then 1 M potassium tert-butoxide (4.0 ml, 0.1 eq.) was added slowly. The resultant mixture was stirred for 45 min. A solution of N-bromosuccinimide (7.83 g, 1.1 eq.) in acetonitrile (50 ml) was added via addition funnel slowly. The orange solution was stirred for 24 hours then the solvent was removed in rotary evaporator to give a residue which was suspended in dichloromethane (50 ml). A 6 N aqueous solution of sodium hydroxide (20 ml) was added and the organic layer was separated and discarded. The aqueous basic layer was acidified with concentrated hydrochloric acid until pH 2 was reached. Dichloromethane (50 ml) was added to extract the acidic aqueous layer. After being separated, the organic layer was washed with brine and concentrated on rotary evaporator to afford the desired product (8 g) as a redish oil in 90% yield.
Data:
$^1$HNMR (CDCl$_3$) δ ppm: 7.1 (s, 1H, aromatic); 6.95 (d, 1H, aromatic); 6.7 (d, 1H, aromatic); 5.15 (s, 1H, OH); 3.9 (s, 3H, OCH$_3$).

Example 2

Preparation of O-Cyclopentyl-(5-bromo-2-methoxy) phenol

To a solution of 5-bromo-2-methoxyphenol (8.0 g, 0.04 mol) in dry N,N-dimethylformamide (50 ml) was added cyclopentyl bromide (4.75 ml, 1.1 eq.) followed by potassium carbonate (6.1 g, 1.1 eq.). The suspension was heated at 120° C. overnight. After 16 hours an additional 2 g of potassium carbonate and 1 ml of cyclopentyl bromide were added. The suspension was stirred at 120° C. for an additional 3 hours. The reaction was allowed to cool at ambient temperature and a 6 N aqueous solution of sodium hydroxide was added followed by ethyl acetate and water. The organic layer was separated and washed with water and brine, dried over magnesium sulfate and filtered under vacuum. The filtrate was concentrated in rotary evaporator to afford the title compound (8 g, 75%).
Data:
$^1$HNMR (CDCl$_3$) δ ppm: 7.0 (1s, 1d, 2H, aromatics); 6.7 (d, 1H, aromatic); 4.7 (m, 1H, C$\underline{H}$—O—phenyl); 3.8 (s, 3H, OCH$_3$); 2.0–1.5 (m, 8H, cyclopentyl).

Example 3

Preparation of 3-(3'-Cyclopentyloxy4'-methoxy) phenyl-2-cyclohexene-1-one.

To a solution of O-cyclopentyl-(5-bromo-2-methoxy)-phenol (400 mg, 1.48 mmol) in dry tetrahydrofuran (2 ml) at −78° C. was added a 2.5 M solution of n-butyllithium (651.2 μL, 1.1 eq.). The mixture was stirred at −78° C. for 15 min., then 3-ethoxy-2-cyclohexen-1-one (200 μL; 1.0 eq.) was added slowly via syringe. The reaction mixture was stirred at −78° C. for 10–15 min. and 1 N aqueous hydrochloric acid was added followed by tert-butylmethyl ether. The organic layer was separated and concentrated in rotary evaporator to afford an oil which was a mixture of the desired product (95% by GC-MS) and excess of 3-ethoxy-2-cyclohexen-1-one (5%). Removal of the latter by distillation under high vacuum, gave the title product (367 mg; 87%) as a solid.
Data:
$^1$HNMR (CDCl$_3$) δ ppm: 7.12 (d, 1H, aromatic); 7.09 (s, 1H, aromatic); 6.85 (d, 1H, aromatic); 6.4 (s, 1H, vinylic); 4.75 (m, 1H, C$\underline{H}$—O—phenyl); 3.85 (s, 3H, OCH$_3$); 2.7 (m, 2H, CH$_2$-cyclohexanone) 2.45 (m, 2H, CH$_2$-cyclohexanone); 2.1 (m, 2H, CH$_2$-cyclohexanone); 2.0–1.5 (m, 8H, cyclopentyl).

Example 4

Preparation of 3-Cyano-3[3'-cyclopentyloxy-4'-methoxy)phenyl-cyclohexan-1-one

To a solution of 3-(3'-cyclopentyloxy-4'-methoxy)phenyl-2-cyclohexene-1-one (367 mg, 1.28 mmol) in N,N-dimethylformamide at room temperature was added water (4 ml), ammonium chloride (trimethylamine hydrochloride can be used instead) (103 mg, 1.5 eq.) and potassium cyanide (167 mg, 2 eq.). The reaction mixture was heated at 110° C.

for 48 hours. Water was then added followed by tert-butylmethyl ether. The organic layer was separated, washed with brine and dried over magnesium sulfate. After filtration under vacuum, the filtrate was concentrated in rotary evaporator to give a crude oil which was purified by flash chromatography (hexanes: ethyl acetate 5: 1) to afford the desired product in 40% yield.

Data:

$^1$HNMR (CDCl$_3$) δ ppm: 6.95 (1d, 1s, 2H, aromatics); 6.85 (d, 1H, aromatic); 4.75 (m, 1H, C<u>H</u>—O—phenyl); 3.85 (s, 3H, OCH$_3$); 2.82 (s, 2H, CH$_2$-cyclohexanone); 2.6–1.5 (m, 14H, cyclopentyl and cyclohexanone).

Example 5

Preparation of 5-Cyano-5[3'-cyclopentyloxy-4'-methoxy)phenyl-2-ethylcarboxylate-cyclohexan-1-one To a solution of 3-cyano-3[3'-cyclopentyloxy-4'-methoxy)phenyl-cyclohexan-1-one (115 mg, 0.367 mmol) in tetrahydrofuran (2 ml) at −78° C. was added lithium N,N-diisopropylamide (250 μL, 1.2 eq.) dropwise. The mixture was stirred at that temperature for 30 min. Chloroethylorthoformate was added dropwise via syringe and the reaction was stirred at −78° C. for 30 min. and then quenched with water. Tert-butylmethyl ether was added and the aqueous layer was separated via separatory funnel. The organic solution was washed with water and brine and concentrated in rotary evaporator to give an oil which upon purification on flash chromatography (hexanes: ethyl acetate 4:1) afforded the title compound (42 mg, 40%).

Data:

$^1$HNMR (CDCl$_3$) δ ppm: 7.0 (m, 2H, aromatics); 6.85 (d, 1H, aromatic); 4.8 (m, 1H, C<u>H</u>—O—phenyl); 4.25 (q, 2H, —CO$_2$—C<u>H</u>$_2$—) 3.85 (s, 3H, OCH$_3$); 2.4–1.5 (m, 14H, cyclopentyl and cyclohexanone); 1.33 (t, 3H, CH$_3$-ester).

Example 6

Preparation of cis-4-Cyano-4-(3-cyclopentyloxy-4-methoxyphenyl)cyclohexane-1-carboxylic acid]

To a solution of 5-cyano-5-[3'-cyclopentyloxy-4'-methoxy)phenyl-2-ethylcarboxylate-cyclohexan-1-one (20 mg, 0.05 mmol) in acetic acid was added platinum dioxide (3 mg). The suspension was set under hydrogen pressure (60 psi) in the PARR shacker overnight. The mixture was then filtered and the filtrate was concentrated in rotary evaporator to give a residue which was purified on prep. TLC plate to yield SB 207499 (6.2 mg, 30%).

Data:

$^1$HNMR (CDCl$_3$) δ ppm: 7.0 (s, 1H, aromatis); 6.95 (d, 1H, aromatic); 6.82 (d, 1H, aromatic); 4.8 (m, 1H, C<u>H</u>—O—phenyl); 3.85 (s, 3H, OCH$_3$); 2.5–1.5 (m, 16H, cyclopentyl and cyclohexanone).

What is claimed is:

1. A process for preparing substituted cyclohexanoic acids of formula (I)

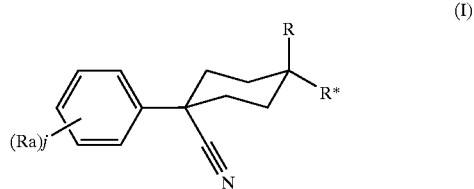

(I)

where $R_a$ is a carbon-containing group optionally linked by oxygen, sulfur or nitrogen to the phenyl ring and j is 1–5; and
one of R and R* is hydrogen and the other is C(O)OH;
which process comprises:
catalytically reducing a ketone of formula II

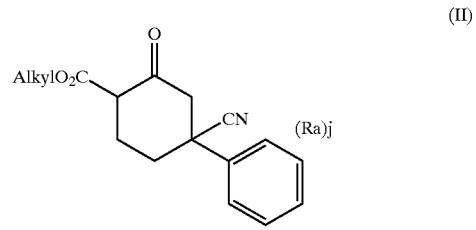

(II)

where alkyl has 1–6 carbon atoms and (Ra)j is the same as defined above, using a heavy metal catalyst and hydrogen gas.

2. The process of claim 1 wherein j is 2 and the Ra groups are substituted at the 3 and 4 positions on the phenyl ring.

3. The process of claim 1 wherein the compound is a compound of formula

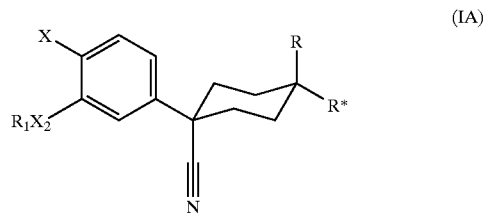

(IA)

wherein:
$R_1$ is —(CR$_4$R$_5$)$_r$R$_6$ wherein the alkyl moieties are unsubstituted or substituted with one or more halogens;
$R_4$ and $R_5$ are independently selected hydrogen or C$_{1-2}$ alkyl;
$R_6$ is hydrogen, methyl, hydroxyl, aryl, halo substituted aryl, aryloxyC$_{1-3}$ alkyl, halo substituted aryloxyC$_{1-3}$ alkyl, indanyl, indenyl, C$_{7-11}$ polycycloalkyl, tetrahydrofuranyl, furanyl, tetrahydropyranyl, pyranyl, tetrahydrothienyl, thienyl, tetrahydrothiopyranyl, thiopyranyl, C$_{3-6}$ cycloalkyl, or a C$_{4-6}$ cycloalkyl, containing one or two unsaturated bonds, wherein the cycloalkyl or heterocyclic moiety is unsubstituted or substituted by 1 to 3 methyl groups, one ethyl group, or an hydroxyl group;
provided that:
b) when R$_6$ is hydroxyl, then r is 2 to 6; or
d) when R$_6$ is 2-tetrahydropyranyl, 2-tetrahydrothiopyranyl, 2-tetrahydrofuranyl, or 2-tetrahydrothienyl, then r is 1 to 6;
X is YR$_2$;
Y is O;

$X_2$ is O;

$R_2$ is —$CH_3$ or —$CH_2CH_3$, unsubstituted or substituted by 1 or more halogens;

one of R and R* is hydrogen and the other is C(O)OH.

4. The process of claim 1 wherein the heavy metal catalyst is platinum oxide.

5. The process of claim 3 wherein in formula (I) $R_1$ is —$CH_2$-cyclopropyl, cyclopentyl, 3-hydroxycyclopentyl, methyl or $CHF_2$ and $R_2$ is $CF_2H$ or $CH_3$.

6. The process of claim 3 wherein $R_1$ is cyclopentyl and $R_2$ is methyl.

* * * * *